US010099636B2

(12) United States Patent
Boesen (10) Patent No.: US 10,099,636 B2
(45) Date of Patent: Oct. 16, 2018

(54) SYSTEM AND METHOD FOR DETERMINING A USER ROLE AND USER SETTINGS ASSOCIATED WITH A VEHICLE (71) Applicant: BRAGI GmbH, München (DE)

(72) Inventor: Peter Vincent Boesen, München (DE)

(*) Notice: Subject to any disclaimer, the term of this patent is extended or adjusted under 35 U.S.C. 154(b) by 0 days.

(21) Appl. No.: 15/356,882

(22) Filed: Nov. 21, 2016

(65) Prior Publication Data
US 2017/0151918 A1 Jun. 1, 2017

Related U.S. Application Data (60) Provisional application No. 62/260,438, filed on Nov. 27, 2015.

(51) Int. Cl.
B60R 16/037 (2006.01)
B60W 40/08 (2012.01)
B60N 2/02 (2006.01)

(52) U.S. Cl.
CPC .......... B60R 16/037 (2013.01); B60N 2/0248 (2013.01); B60W 40/08 (2013.01); B60W 2040/0809 (2013.01); B60W 2040/0872 (2013.01); B60W 2040/0881 (2013.01)

(58) Field of Classification Search
USPC .......... 701/48; 713/186; 340/5.52, 5.81, 5.82
See application file for complete search history.

(56) References Cited

U.S. PATENT DOCUMENTS 3,934,100 A 1/1976 Harada
4,150,262 A 4/1979 Ono
4,334,315 A 6/1982 Ono et al.
4,375,016 A 2/1983 Harada
4,588,867 A 5/1986 Konomi
4,654,883 A 3/1987 Iwata
4,682,180 A 7/1987 Gans
(Continued)

FOREIGN PATENT DOCUMENTS

CN 204244472 U 4/2015
CN 104837094 A 8/2015
(Continued)

OTHER PUBLICATIONS

Announcing the $3,333,333 Stretch Goal (Feb. 24, 2014).
(Continued)

Primary Examiner — Richard A Goldman
(74) Attorney, Agent, or Firm — Goodhue, Coleman & Owens, P.C.

(57) ABSTRACT

A system includes a vehicle, the vehicle comprising a vehicle network. The system further includes a wireless earpiece worn by a user in operative communication with the vehicle network. The vehicle is configured to determine a role of the user and user settings for the vehicle from data received from the wireless earpiece and implement the user settings for the vehicle. A method for adjusting user settings associated with a vehicle based on data from a wireless earpiece includes acquiring user data from a wireless earpiece worn by a user at a vehicle, based on the user data, determining by the vehicle one or more user settings and a role of the user, and automatically adjusting by the vehicle of one or more vehicle features based on the one or more user settings in accordance with the role of the user.

15 Claims, 6 Drawing Sheets

(56) References Cited

U.S. PATENT DOCUMENTS

| | | |
|---|---|---|
| 4,791,673 A | 12/1988 | Schreiber |
| 4,865,044 A | 9/1989 | Wallace et al. |
| 5,191,602 A | 3/1993 | Regen et al. |
| 5,201,007 A | 4/1993 | Ward et al. |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart |
| 5,363,444 A | 11/1994 | Norris |
| 5,497,339 A | 3/1996 | Bernard |
| 5,606,621 A | 2/1997 | Reiter et al. |
| 5,613,222 A | 3/1997 | Guenther |
| 5,692,059 A | 11/1997 | Kruger |
| 5,721,783 A | 2/1998 | Anderson |
| 5,749,072 A | 5/1998 | Mazurkiewicz et al. |
| 5,771,438 A | 6/1998 | Palermo et al. |
| 5,802,167 A | 9/1998 | Hong |
| 5,929,774 A | 7/1999 | Charlton |
| 5,933,506 A | 8/1999 | Aoki et al. |
| 5,949,896 A | 9/1999 | Nageno et al. |
| 5,987,146 A | 11/1999 | Pluvinage et al. |
| 6,021,207 A | 2/2000 | Puthuff et al. |
| 6,041,410 A | 3/2000 | Hsu et al. |
| 6,048,324 A | 4/2000 | Socci et al. |
| 6,054,989 A | 4/2000 | Robertson et al. |
| 6,081,724 A | 6/2000 | Wilson |
| 6,094,492 A | 7/2000 | Boesen |
| 6,111,569 A | 8/2000 | Brusky et al. |
| 6,112,103 A | 8/2000 | Puthuff |
| 6,140,939 A | 10/2000 | Flick |
| 6,157,727 A | 12/2000 | Rueda |
| 6,167,039 A | 12/2000 | Karlsson et al. |
| 6,181,801 B1 | 1/2001 | Puthuff et al. |
| 6,208,372 B1 | 3/2001 | Barraclough |
| 6,275,789 B1 | 8/2001 | Moser et al. |
| 6,339,754 B1 | 1/2002 | Flanagan et al. |
| 6,408,081 B1 | 6/2002 | Boesen |
| D464,039 S | 10/2002 | Boesen |
| 6,470,893 B1 | 10/2002 | Boesen |
| 6,472,978 B1 | 10/2002 | Takagi et al. |
| D468,299 S | 1/2003 | Boesen |
| D468,300 S | 1/2003 | Boesen |
| 6,542,721 B2 | 4/2003 | Boesen |
| 6,560,468 B1 | 5/2003 | Boesen |
| 6,654,721 B2 | 11/2003 | Handelman |
| 6,664,713 B2 | 12/2003 | Boesen |
| 6,694,180 B1 | 2/2004 | Boesen |
| 6,718,043 B1 | 4/2004 | Boesen |
| 6,738,485 B1 | 5/2004 | Boesen |
| 6,748,095 B1 | 6/2004 | Goss |
| 6,754,358 B1 | 6/2004 | Boesen et al. |
| 6,784,873 B1 | 8/2004 | Boesen et al. |
| 6,823,195 B1 | 11/2004 | Boesen |
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,952,483 B2 | 10/2005 | Boesen et al. |
| 6,987,986 B2 | 1/2006 | Boesen |
| 7,136,282 B1 | 11/2006 | Rebeske |
| 7,203,331 B2 | 4/2007 | Boesen |
| 7,209,569 B2 | 4/2007 | Boesen |
| 7,215,790 B2 | 5/2007 | Boesen et al. |
| 7,463,902 B2 | 12/2008 | Boesen |
| 7,508,411 B2 | 3/2009 | Boesen |
| 7,983,628 B2 | 7/2011 | Boesen |
| 8,108,143 B1 | 1/2012 | Tester |
| 8,140,357 B1 | 3/2012 | Boesen |
| 8,610,585 B1 | 12/2013 | Kielbasa et al. |
| 8,855,918 B2 | 10/2014 | Ranford et al. |
| 8,994,498 B2 * | 3/2015 | Agrafioti ............... G06F 21/40 340/5.52 |
| 9,037,125 B1 * | 5/2015 | Kadous ............ H04M 1/72577 455/418 |
| 9,081,944 B2 * | 7/2015 | Camacho ............... G06F 21/31 |
| 9,272,711 B1 * | 3/2016 | Sivaraman ............ G08G 1/166 |
| 9,510,159 B1 * | 11/2016 | Cuddihy ............... H04W 4/046 |
| 9,638,537 B2 | 5/2017 | Abramson et al. |
| 9,741,010 B1 | 8/2017 | Heinla |
| 9,805,437 B2 | 10/2017 | Mun et al. |
| 9,869,556 B2 | 1/2018 | Jung et al. |
| 2001/0005197 A1 | 6/2001 | Mishra et al. |
| 2001/0025222 A1 | 9/2001 | Bechtolsheim et al. |
| 2001/0027121 A1 | 10/2001 | Boesen |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0002705 A1 * | 1/2003 | Boesen ............... H04M 1/6066 381/380 |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0124968 A1 * | 7/2004 | Inada .................. B60R 25/2081 340/5.72 |
| 2004/0160511 A1 | 8/2004 | Boesen |
| 2005/0017842 A1 * | 1/2005 | Dematteo .......... G07C 9/00309 340/5.72 |
| 2005/0043056 A1 | 2/2005 | Boesen |
| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0251455 A1 | 11/2005 | Boesen |
| 2005/0266876 A1 | 12/2005 | Boesen |
| 2006/0029246 A1 | 2/2006 | Boesen |
| 2006/0074671 A1 | 4/2006 | Farmaner et al. |
| 2006/0074808 A1 | 4/2006 | Boesen |
| 2006/0220915 A1 | 10/2006 | Bauer |
| 2007/0127734 A1 | 6/2007 | Brulle-Drews |
| 2008/0001780 A1 | 1/2008 | Ohno et al. |
| 2008/0146890 A1 | 6/2008 | LeBoeuf et al. |
| 2008/0254780 A1 | 10/2008 | Kuhl et al. |
| 2009/0002197 A1 | 1/2009 | Cemper |
| 2009/0003620 A1 | 1/2009 | McKillop et al. |
| 2009/0128286 A1 | 5/2009 | Vitito |
| 2009/0191920 A1 | 7/2009 | Regen et al. |
| 2009/0238386 A1 | 9/2009 | Usher et al. |
| 2010/0033313 A1 | 2/2010 | Keady et al. |
| 2010/0210212 A1 | 8/2010 | Sato |
| 2011/0090093 A1 | 4/2011 | Grimm et al. |
| 2011/0215921 A1 * | 9/2011 | Ben Ayed ............... G08B 1/08 340/539.11 |
| 2011/0227812 A1 | 9/2011 | Haddick et al. |
| 2012/0075168 A1 | 3/2012 | Osterhout et al. |
| 2012/0194418 A1 | 8/2012 | Osterhout et al. |
| 2013/0090744 A1 * | 4/2013 | Tran ..................... G05B 11/01 700/9 |
| 2013/0322667 A1 | 12/2013 | Christensen |
| 2013/0329051 A1 | 12/2013 | Boesen |
| 2014/0122092 A1 | 5/2014 | Goldstein |
| 2014/0163771 A1 * | 6/2014 | Demeniuk ............. H04B 1/082 701/2 |
| 2014/0185828 A1 | 7/2014 | Helbling |
| 2014/0270227 A1 | 9/2014 | Swanson |
| 2014/0309806 A1 | 10/2014 | Ricci |
| 2015/0028996 A1 * | 1/2015 | Agrafioti ................ G06F 21/40 340/5.82 |
| 2015/0035685 A1 * | 2/2015 | Strickland ............. B60Q 9/008 340/901 |
| 2015/0057839 A1 * | 2/2015 | Chang .................. B60R 16/037 701/2 |
| 2015/0066678 A1 | 3/2015 | Ogilvie |
| 2015/0095122 A1 | 4/2015 | Eramian |

(56) References Cited

U.S. PATENT DOCUMENTS

| | | | |
|---|---|---|---|
| 2015/0095197 A1 | 4/2015 | Eramian | |
| 2015/0095198 A1 | 4/2015 | Eramian | |
| 2015/0148989 A1* | 5/2015 | Cooper | B60R 16/037 701/2 |
| 2015/0149042 A1 | 5/2015 | Cooper | |
| 2015/0243172 A1* | 8/2015 | Eskilson | A61B 5/18 701/1 |
| 2015/0350413 A1 | 12/2015 | Ma et al. | |
| 2015/0379859 A1* | 12/2015 | Nespolo | G08B 21/24 340/539.32 |
| 2016/0001781 A1* | 1/2016 | Fung | G06F 19/345 701/36 |
| 2016/0016513 A1 | 1/2016 | Censo et al. | |
| 2016/0033280 A1 | 2/2016 | Moore et al. | |
| 2016/0061613 A1 | 3/2016 | Jung et al. | |
| 2016/0069699 A1 | 3/2016 | Chen et al. | |
| 2016/0125677 A1* | 5/2016 | Williams | G07C 9/00111 340/5.81 |
| 2016/0169688 A1 | 6/2016 | Kweon et al. | |
| 2016/0182757 A1 | 6/2016 | Yoo | |
| 2016/0182762 A1 | 6/2016 | Eum | |
| 2016/0191511 A1* | 6/2016 | Tijerina | H04L 63/0853 726/7 |
| 2016/0210752 A1* | 7/2016 | Ratcliff | G09G 5/026 |
| 2016/0227009 A1* | 8/2016 | Kim | B60K 35/00 |
| 2016/0335454 A1 | 11/2016 | Choe et al. | |
| 2017/0061751 A1 | 3/2017 | Loermann et al. | |
| 2017/0094467 A1 | 3/2017 | Kiuchi et al. | |
| 2017/0108346 A1 | 4/2017 | Cho et al. | |
| 2017/0112671 A1 | 4/2017 | Goldstein | |
| 2017/0151918 A1* | 6/2017 | Boesen | B60R 16/037 |
| 2017/0153114 A1* | 6/2017 | Boesen | G01C 21/3423 |
| 2017/0153636 A1* | 6/2017 | Boesen | G05D 1/0016 |
| 2017/0206218 A1 | 7/2017 | Jai et al. | |
| 2017/0208052 A1 | 7/2017 | Jai et al. | |
| 2017/0208125 A1 | 7/2017 | Jai et al. | |
| 2017/0228105 A1 | 8/2017 | Varadarajan | |
| 2017/0289168 A1* | 10/2017 | Bar | H04L 63/0853 |
| 2017/0357329 A1 | 12/2017 | Park et al. | |
| 2017/0357381 A1 | 12/2017 | Santo et al. | |
| 2017/0361133 A1 | 12/2017 | Yu et al. | |
| 2018/0013897 A1 | 1/2018 | Kumar et al. | |
| 2018/0017405 A1 | 1/2018 | Chen et al. | |

FOREIGN PATENT DOCUMENTS

| | | |
|---|---|---|
| DE | 10253192 A1 | 5/2004 |
| DE | 10334203 A1 | 3/2005 |
| DE | 102010003429 A1 | 10/2011 |
| DE | 102011118966 A1 | 5/2013 |
| EP | 1017252 A2 | 7/2000 |
| EP | 1469659 A1 | 10/2004 |
| GB | 2074817 | 4/1981 |
| JP | 06292195 | 10/1998 |
| WO | 2008103925 A1 | 8/2008 |
| WO | 2007034371 A3 | 11/2008 |
| WO | 2011001433 A2 | 1/2011 |
| WO | 2012071127 A1 | 5/2012 |
| WO | 2013134956 A1 | 9/2013 |
| WO | 2014043179 A2 | 3/2014 |
| WO | 2014046602 A1 | 3/2014 |
| WO | 2015061633 A2 | 4/2015 |
| WO | 2015110577 A1 | 7/2015 |
| WO | 2015110587 A1 | 7/2015 |
| WO | 2016032990 A1 | 3/2016 |
| WO | 2017034287 A1 | 3/2017 |

OTHER PUBLICATIONS

BRAGI is on Facebook (2014).
BRAGI Update—Arrival of Prototype Chassis Parts—More People—Awesomeness (May 13, 2014).
BRAGI Update—Chinese New Year, Design Verification, Charging Case, More People, Timeline(Mar. 6, 2015).
BRAGI Update—First Sleeves From Prototype Tool—Software Development Kit (Jun. 5, 2014).
BRAGI Update—Let's Get Ready to Rumble, A Lot to Be Done Over Christmas (Dec. 22, 2014).
BRAGI Update—Memories From April—Update on Progress (Sep. 16, 2014).
BRAGI Update—Memories from May—Update on Progress—Sweet (Oct. 13, 2014).
BRAGI Update—Memories From One Month Before Kickstarter—Update on Progress (Jul. 10, 2014).
BRAGI Update—Memories From the First Month of Kickstarter—Update on Progress (Aug. 1, 2014).
BRAGI Update—Memories From the Second Month of Kickstarter—Update on Progress (Aug. 22, 2014).
BRAGI Update—New People @BRAGI—Prototypes (Jun. 26, 2014).
BRAGI Update—Office Tour, Tour to China, Tour to CES (Dec. 11, 2014).
BRAGI Update—Status on Wireless, Bits and Pieces, Testing-Oh Yeah, Timeline(Apr. 24, 2015).
BRAGI Update—The App Preview, The Charger, The SDK, BRAGI Funding and Chinese New Year (Feb. 11, 2015).
BRAGI Update—What We Did Over Christmas, Las Vegas & CES (Jan. 19, 2014).
BRAGI Update—Years of Development, Moments of Utter Joy and Finishing What We Started(Jun. 5, 2015).
BRAGI Update—Alpha 5 and Back to China, Backer Day, on Track(May 16, 2015).
BRAGI Update—Beta2 Production and Factory Line(Aug. 20, 2015).
BRAGI Update—Certifications, Production, Ramping Up (Nov. 13, 2015).
BRAGI Update—Developer Units Shipping and Status(Oct. 5, 2015).
BRAGI Update—Developer Units Started Shipping and Status (Oct. 19, 2015).
BRAGI Update-Developer Units, Investment, Story and Status(Nov. 2, 2015).
BRAGI Update—Getting Close(Aug. 6, 2014).
BRAGI Update—On Track, Design Verification, How It Works and What's Next(Jul. 15, 2015).
BRAGI Update—On Track, on Track and Gems Overview (Jun. 24, 2015).
BRAGI Update—Status on Wireless, Supply, Timeline and Open House@BRAGI(Apr. 1, 2015).
BRAGI Update—Unpacking Video, Reviews on Audio Perform and Boy Are We Getting Close(Sep. 10, 2015).
Last Push Before the Kickstarter Campaign Ends on Monday 4pm CET (Mar. 28, 2014).
Nigel Whitfield: "Fake tape detectors, 'from the stands' footle and UGH? Internet of Things in my set-top box"; http://www.theregister.co.uk/2014/09/24/ibc_round_up_object_audio_dlna_iot/ (Sep. 24, 2014).
Staab, Wayne J., et al., "A One-Size Disposable Hearing Aid is Introduced", The Hearing Journal 53(4):36-41) Apr. 2000.
Stretchgoal—It's Your Dash (Feb. 14, 2014).
Stretchgoal—The Carrying Case for the Dash (Feb. 12, 2014).
Stretchgoal—Windows Phone Support (Feb. 17, 2014).
The Dash + The Charging Case & The BRAGI News (Feb. 21, 2014).
The Dash—A Word From Our Software, Mechanical and Acoustics Team + An Update (Mar. 11, 2014).
Update From BRAGI—$3,000,000—Yipee (Mar. 22, 2014).
Akkermans, "Acoustic Ear Recognition for Person Identification", Automatic Identification Advanced Technologies, 2005 pp. 219-223.
International Search Report & Written Opinion, PCT/EP2016/078800 (dated Feb. 21, 2017).
International Search Report & Written Opinion, PCT/EP16/78790 (dated Apr. 4, 2017).
International Search Report & Written Opinion, PCT/EP2016/078795 (dated Feb. 23, 2017).

(56) References Cited

OTHER PUBLICATIONS

International Search Report & Written Opinion, PCT/EP2016/078796 (dated Feb. 23, 2017).
International Search Report & Written Opinion, PCT/EP2016/078797 (dated Feb. 28, 2017).
International Search Report & Written Opinion, PCT/EP2016/078798 (dated Mar. 10, 2017).
International Search Report & Written Opinion, PCT/EP2016/078799 (dated Mar. 1, 2017).
International Search Report & Written Opinion, PCT/EP2016/078801 (dated Mar. 1, 2017).
BMW, "BMW introduces BMW Connected—The personalized digital assistant", "http://bmwblog.com/2016/01/05/bmw-introduces-bmw-connected-the-personalized-digital-assistant", (Jan. 5, 2016).
Hyundai Motor America, "Hyundai Motor Company Introduces a Health + Mobility Concept for Wellness in Mobility", Fountain Valley, Californa (2017).

\* cited by examiner

SYSTEM AND METHOD FOR DETERMINING A USER ROLE AND USER SETTINGS ASSOCIATED WITH A VEHICLE

PRIORITY STATEMENT

This application claims priority to U.S. Provisional Patent Application 62/260,438, filed on Nov. 27, 2015, and entitled Vehicle with wearable to provide intelligent user settings, hereby incorporated by reference in its entirety.

FIELD OF THE INVENTION

The present invention relates to vehicles. More particularly, but not exclusively, the present invention relates to a vehicle which integrates with or communicates with wearable devices and provides for identifying the role of users associated with the wearable devices.

BACKGROUND

Vehicles may come with various types of electronics packages. These packages may be standard or optional and include electronics associated with communications or entertainment. However, there are various problems and deficiencies with such offerings. What is needed are vehicles with improved electronics options which create, improve, or enhance safety and overall experience of vehicles. In particular, what is needed are vehicles which integrate with wearable devices.

SUMMARY

Therefore, it is a primary object, feature, or advantage of the present invention to improve over the state of the art.

It is another object, feature, or advantage of the present invention to communicate between vehicle systems and wearable devices.

It is a further object, feature, or advantage of the present invention to use wearable devices to increase safety in vehicles.

It is a still further object, feature, or advantage of the present invention to allow a user to control one or more functions of a vehicle using one or more wearable devices such as ear pieces, watches, or glasses.

It is a still further object, feature, or advantage of the present invention to allow a vehicle to identify a driver based on the presence of a particular wearable device.

It is a still further object, feature, or advantage of the present invention to allow a vehicle to identify one or more passengers of a vehicle based on the presence of particular wearable devices.

Another object, feature, or advantage of the present invention is to allow a vehicle to identify not just a user but also the role of the user such as whether the user is a driver or passenger.

Yet another object, feature, or advantage of the present invention is to allow for adjustment of user settings once a user has been identified.

A further object, feature, or advantage of the present invention is to allow for a passenger to adjust different settings than a driver once the user(s) and their roles have been identified.

Yet another object, feature, or advantage of the present invention is to allow a vehicle to obtain biometric information about a driver or passenger using one or more wearable devices.

It is another object, feature, or advantage of the present invention to enhance an existing vehicle through addition of a wearable device.

One or more of these and/or other objects, features, or advantages of the present invention will become apparent from the specification and claims that follow. No single embodiment need provide each and every object, feature, or advantage. Different embodiments may have different objects, features, or advantages. Therefore, the present invention is not to be limited to or by any objects, features, or advantages stated herein.

According to one aspect, a system includes a vehicle, the vehicle comprising a control system and a wireless transceiver operatively connected to the control system. The control system is configured to wirelessly communicate with a wearable device worn by a user using the wireless transceiver and the control system is configured to receive input from one or more sensors of the wearable device.

According to one aspect a system is provided. The system includes a vehicle, the vehicle includes a vehicle network and a wearable device in operative communication with the vehicle network, the wearable device including one or more sensors for receiving sensor data. The system is configured to determine a role of a user of the wearable device within the vehicle. The role of the user may be determined either by the wearable device or the vehicle. The role may be that of a driver or a passenger or based on seat location within the vehicle. Access rights may be assigned to the user based on their role. The system may also be configured to determine an identity of the user. The access rights may be assigned to take into account both the role of the user and the identity of the users and may also take into account other individuals within the vehicle when making this determination. The vehicle may be configured to automatically adjust one or more user settings based on the identity of the user and the role of the user. Example of such user settings may include seat adjustment settings, entertainment system settings, rear view mirror settings, temperature control settings, navigation system settings including saved locations. The wearable device may be one or more earpieces, a watch, glasses, or other types of wearable devices. The wearable device may include an inertial sensor and the vehicle may correlate sensor data from the inertial sensor to an interaction with the vehicle to determine the role of the user. Examples of interactions may include opening a door or touching a steering wheel or other part of a vehicle. The wearable device may include a first wireless ear piece and a second wireless ear pieces each with a wireless transceiver and the system may be configured to determine the role of the user by locating the user within the vehicle by using a signal from the first transceiver and a signal from the second transceiver.

According to another aspect, a method for identifying a role of one or more users within a vehicle is provided. The method may include identifying one or more users within the vehicle based on data from wearable devices and identifying roles of one or more of the users within the vehicle using the wearable. The method may further include adjusting one or more vehicle settings based on identity and role of the one or more users.

According to one aspect a system includes a vehicle, the vehicle having a vehicle network. The system further includes a wearable device in operative communication with the vehicle network. The vehicle is configured to determine user settings for the vehicle from data received from the wearable device and implement the user settings for the vehicle. The data may be biometric data such as biometric determined using one or more sensors of the wearable device such as a physiological sensor or inertial data. The biometric data may also be stored on the wearable device. The user settings may include settings such as steering wheel settings, seat settings, environmental control settings, and entertainment settings.

According to another aspect, a method for adjusting user settings associated with a vehicle based on data from a wearable device is provided. The method includes acquiring user data from a wearable device at a vehicle and based on the user data, determining by the vehicle one or more user settings. The method may further include automatically adjusting by the vehicle of one or more vehicle features based on the one or more user settings. The acquiring user data from the wearable device at a vehicle may be performed by operatively communicating the user data over a wireless linkage between the wearable device and the vehicle. The data may be biometric data. The user settings may include any number of settings include seat position settings and entertainment system settings such as radio presets. The wearable device may include a physiological sensor and/or an inertial sensor.

BRIEF DESCRIPTION OF THE DRAWINGS

FIG, 5 is a flow diagram illustrating one example of a method for determining user identity and/or user role.

DETAILED DESCRIPTION

Some of the most important factors in selecting a vehicle such as car may be the technology available to enhance the experience. This may be of particular importance in certain vehicle segments such as for luxury vehicles. Another important factor in selecting a vehicle may be the available safety features. According to various aspects, the present invention allows for wearable devices including ear pieces to enhance the experience of vehicles and according to some aspects, the present invention allows for wearable devices such as earpieces to enhance the overall safety of the vehicle. Therefore, it is expected that the technology described herein will make any vehicle so equipped more desirable to customers, more satisfying to customers, and potentially more profitable for the vehicle manufacturer. Similarly at least some of the various aspects may be added to existing vehicles as after-market accessories to improve the safety or experience of existing vehicles.

Figure 1:
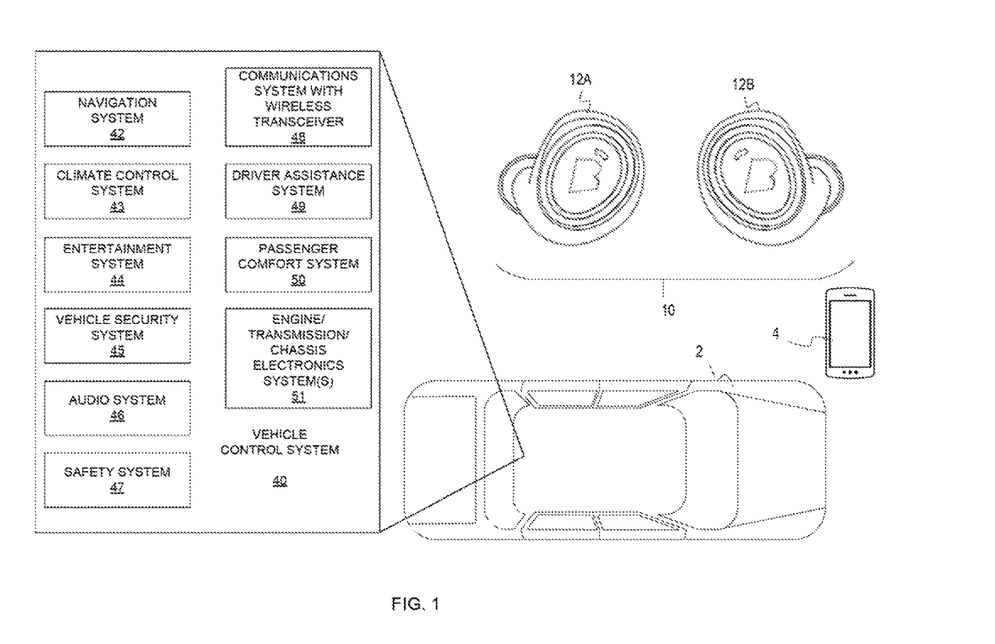
FIG. 1 illustrates one example of a vehicle which integrates with wearable technology.

FIG. 1 illustrates one example of use of a wearable device in conjunction with a vehicle. A shown in FIG. 1 there is a vehicle 2. Although the vehicle shown is a full-size sedan, it is contemplated that the vehicle may be of any number of types of cars, trucks, sport utility vehicles, vans, mini-vans, automotive vehicles, commercial vehicles, agricultural vehicles, construction vehicles, specialty vehicles, recreational vehicles, buses, motorcycles, aircraft, boats, ships, yachts, spacecraft, or other types of vehicles. The vehicle may be gas-powered, diesel powered, electric, solar-powered, or human-powered. The vehicle may be actively operated by a driver or may be partially or completely autonomous or self-driving. The vehicle 2 may have a vehicle control system 40. The vehicle control system is a system which may include any number of mechanical and electromechanical subsystems. As shown in FIG. 1, such systems may include a navigation system 42, an entertainment system 44, a vehicle security system 45, an audio system 46, a safety system 47, a communications system 48 preferably with a wireless transceiver, a driver assistance system 49, a passenger comfort system 50, and an engine/transmission, chassis electronics system(s) 51. Of course, other examples of vehicle control sub-systems are contemplated. In addition, it is to be understood that there may be overlap between some of these different vehicle systems and the presence or absence of these vehicle systems as well as other vehicle systems may depend upon the type of vehicle, the type of fuel or propulsion system, the size of the vehicle, and other factors and variables. In the automotive context, examples of the driver assistance system 49 may include one or more subsystems such as a lane assist system, a speed assist system, a blind spot detection system, a park assist system, and an adaptive cruise control system. In the automotive context, examples of the passenger comfort system 50 may include one or more subsystems such as automatic climate control, electronic seat adjustment, automatic wipers, automatic headlamps, and automatic cooling. In the automotive context, examples of the safety system 47 may include active safety systems such as air bags, hill descent control, and an emergency brake assist system. Aspects of the navigation system 42, the entertainment system 44, the audio system 46, and the communications system 48 may be combined into an infotainment system.

One or more wearable devices such as a set of earpieces 10 including a left earpiece 12A and a right earpiece 12B may in operative communication with the vehicle control system 40 such as through the communication system 48. For example, the communication system 48 may provide a Bluetooth or BLE or Wi-Fi link to wearable devices or may otherwise provide for communications with the wearable devices preferably through wireless communications. The vehicle 2 may communicate with the wearable device(s) directly, or alternatively, or in addition, the vehicle 2 may communicate with the wearable device(s) through an intermediary device such as a mobile device 4 which may be a mobile phone, a tablet, or other type of mobile device or other computing device.

As will be explained in further details with respect to various examples, the wearable device(s) 10 interact with the vehicle control system 40 in any number of different ways. For example, the wearable device(s) 10 may provide sensor data, identity information, stored information, streamed information, or other types of information to the vehicle. Based on this information, the vehicle may take any number of actions which may include one or more actions taken by the vehicle control system (or subsystems thereof). In addition, the vehicle 2 may communicate sensor data, identity information, stored information, streamed information or other types of information to the wearable device(s) 10.

Figure 2:
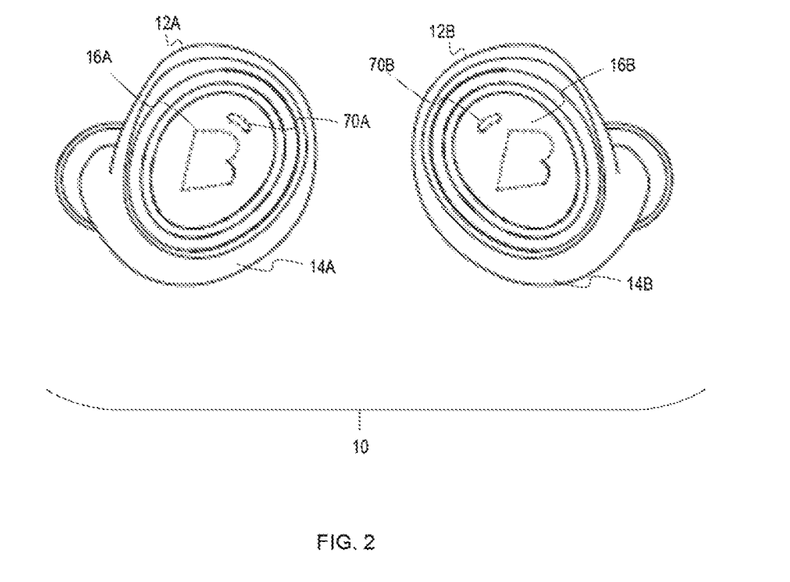
FIG. 2 illustrates one example of a set of wearable devices in the form of ear pieces.

FIG. 2 illustrates one example of a wearable device in the form of a set of ear pieces 10 in greater detail. FIG. 1 illustrates a set of earpiece wearables 10 which includes a let earpiece 12A and a right earpiece 12B. Each of the earpieces wearables 12A, 12B has an earpiece wearable housing 14A, 14B which may be in the form of a protective shell or casing and may be an in-the-ear earpiece housing. A left infrared through ultraviolet spectrometer 16A and right infrared through ultraviolet spectrometer 16B is also shown. Each earpiece 12A, 12B may include one or more microphones 70A, 70B. Note that the air microphones 70A, 70B are outward facing such that the air microphones 70A, 70B may capture ambient environmental sound. It is to be understood that any number of microphones may be present including air conduction microphones, bone conduction microphones, or other audio sensors.

Figure 3:
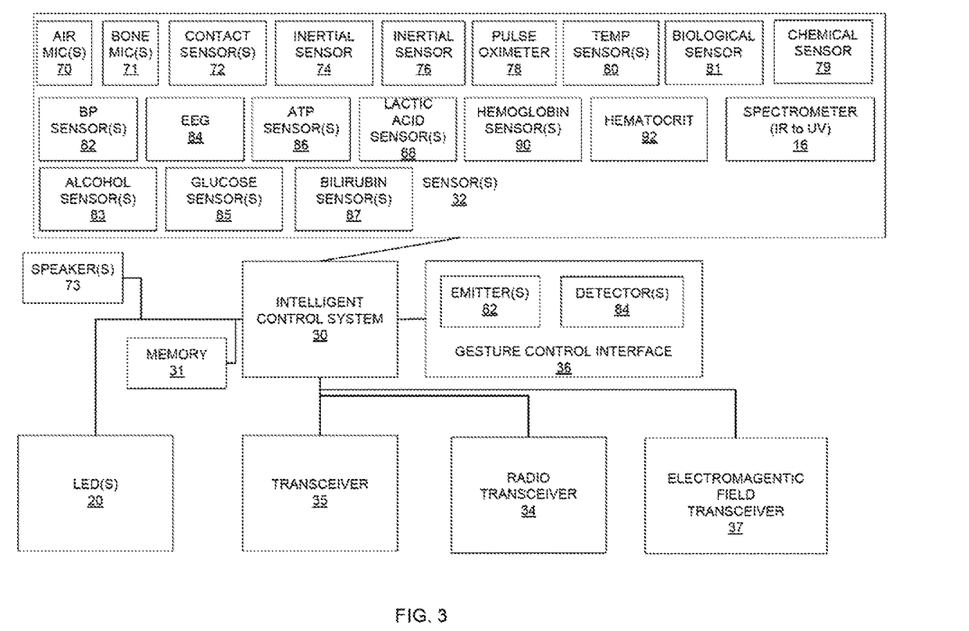
FIG. 3 is a block diagram of one example of a wearable device in the form of an earpiece.

FIG. 3 is a block diagram illustrating a device. The device may include one or more LEDs 20 electrically connected to an intelligent control system 30. The intelligent control system 30 may include one or more processors, microcontrollers, application specific integrated circuits, or other types of integrated circuits. The intelligent control system 30 may also be electrically connected to one or more sensors 32. Where the device is an earpiece, the sensor(s) may include an inertial sensor 74, another inertial sensor 76. Each inertial sensor 74, 76 may include an accelerometer, a gyro sensor or gyrometer, a magnetometer or other type of inertial sensor. The sensor(s) 32 may also include one or more contact sensors 72, one or more bone conduction microphones 71, one or more air conduction microphones 70, one or more chemical sensors 79, a pulse oximeter 76, a temperature sensor 80, or other physiological or biological sensor(s). Further examples of physiological or biological sensors include an alcohol sensor 83, glucose sensor 85, or bilirubin sensor 87. Other examples of physiological or biological sensors may also be included in the device. These may include a blood pressure sensor 82, an electroencephalogram (EEG) 84, an Adenosine Triphosphate (ATP) sensor, a lactic acid sensor 88, a hemoglobin sensor 90, a hematocrit sensor 92 or other biological or chemical sensor.

A spectrometer 16 is also shown. The spectrometer 16 may be an infrared (IR) through ultraviolet (UV) spectrometer although it is contemplated that any number of wavelengths in the infrared, visible, or ultraviolet spectrums may be detected. The spectrometer 16 is preferably adapted to measure environmental wavelengths for analysis and recommendations and thus preferably is located on or at the external facing side of the device.

A gesture control interface 36 is also operatively connected to or integrated into the intelligent control system 30. The gesture control interface 36 may include one or more emitters 82 and one or more detectors 84 for sensing user gestures. The emitters may be of any number of types including infrared LEDs. The device may include a transceiver 35 which may allow for induction transmissions such as through near field magnetic induction. A short range transceiver 34 using Bluetooth, BLE, UWB, or other means of radio communication may also be present. The short range transceiver 34 may be used to communicate with the vehicle control system. In operation, the intelligent control system 30 may be configured to convey different information using one or more of the LED(s) 20 based on context or mode of operation of the device. The various sensors 32, the intelligent control system 30, and other electronic components may be located on the printed circuit board of the device. One or more speakers 73 may also be operatively connected to the intelligent control system 30. A memory 31 is shown. The memory 31 may be used for various purposes. This may including storage of biometric information, storage of user settings, or other data.

An electromagnetic (E/M) field transceiver 37 or other type of electromagnetic field receiver is also operatively connected to the intelligent control system 30 to link the intelligent control system 30 to the electromagnetic field of the user. The use of the E/M transceiver 37 allows the device to link electromagnetically into a personal area network or body area network or other device.

According to another aspect, earpiece wearables may be used to identify one or more users. Each earpiece wearable may include its own identifier. In addition, each earpiece may be used to determine or confirm identity of an individual wearing it. This may be accomplished in various ways including through voice imprint. In particular, an individual may speak and their voice analyzed by the earpiece and compared to known samples or metrics related to characteristics such as pitch, tone, cadence, and frequency in order to identify the individual. Alternatively, identify may be established through other biometric information collected by the earpiece including based on movements such as gait collected with the inertial sensor or heart rate variability.

Other types of user identification, and authentication may also be used. For example, an individual may be asked to specify other information to the earpiece in order to confirm identity. This may include answering specific questions. For example, the ear piece may ask multiple questions with yes or no or multiple choice answers which the correct individual will know but others are not likely to know. These questions may be stored within a database and are questions which the individual specifically provided answers. These questions may also be based on activities of the user which are stored on the earpiece or are retrievable from a system in operative communication with the ear piece. These may include information about physical activities, locations, or other activities.

Alternatively, instead of the earpiece performing the analysis associated with user identification and authentication, necessary information such as voice samples or voice or gestural responses of biometric information may be collected by the ear piece and communicated to the vehicle, mobile device, or other device for performing the analysis.

Once a user has been identified the user may be authorized to perform various functions in various ways. For example, the vehicle may be unlocked such, as by a person saying "unlock" or the vehicle may be remote started and environmental controls set by a person saying "start my car and set temperature to 72 degrees." These actions may be taken by the vehicle control system or its subsystems such as an access and security subsystem or a climate control subsystem. In addition, actions may be taken based on proximity of the individual to the user or based on other contextual information.

Various types of vehicle controls may be a part of the vehicle access and security subsystems. These may include actuators such as actuators associated with door locks or locks associated with other compartments. Other types of vehicle controls may include an ignition lock switch which may be unlocked or locked. Other types of vehicle controls may include actuators associated with windows, in addition to these functions, any number of different vehicle functions may be performed. The vehicle functions performed by a properly identified individual may be the same types of vehicle functions that an individual may perform as a driver of the vehicle. Other types of vehicle controls may include any number of settings such as audio system settings, temperature control settings, entertainment system settings, navigation settings, or other types of settings.

Figure 4:
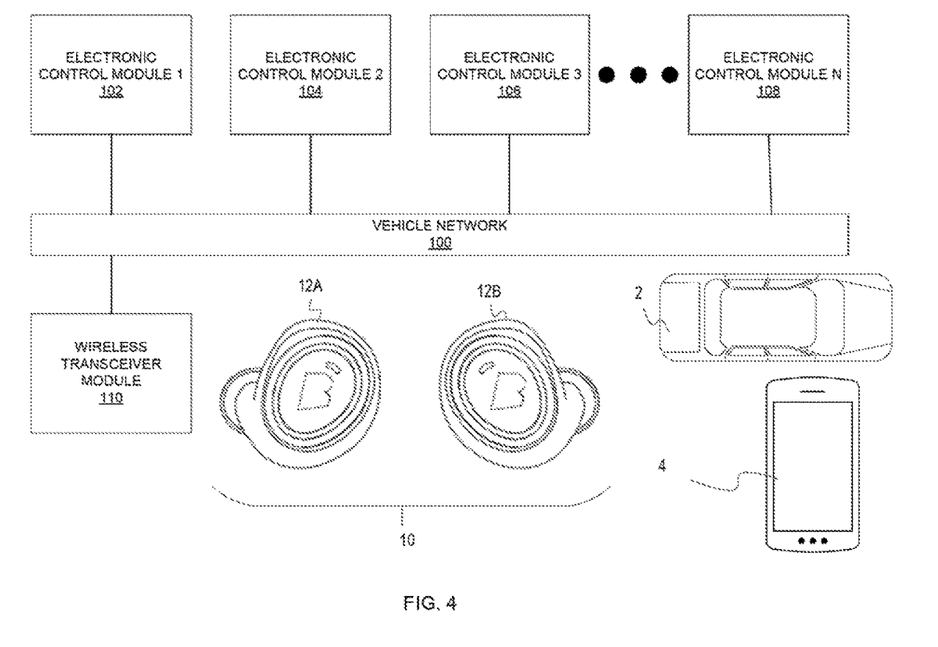
FIG. 4 is a diagram of wearable devices communicating with a vehicle network.

FIG. 4 illustrates another example. In FIG. 4, a vehicle network 100 is shown. According to one aspect, the wearable devices 12A, 12B may communicate information through a vehicle network 100 associated with a vehicle 2. Thus, once an identity of a user has been established, commands may be communicated over the vehicle network 100 or vehicle bus to perform one or more vehicle functions. Protocols which are used may include a Controller Area Network (CAN), Local Interconnect Network (LIN), or others including proprietary network protocols or network protocol overlays.

Various types of electronic control modules 102, 104, 106, 108 or electronic control units may communicate over the network 100 of the vehicle. These may include electronic modules such as an engine control unit (ECU), a transmission control unit (TCU), an anti-lock braking system (ABS), a body control module (BCM), a door control unit (DCU), an electric power steering control unit (PSCU), a human-machine interface (HMI), powertrain control module (PCM), speed control unit (SCU), telematic control unit (TCU), brake control unit (BCM), battery management system, and numerous others. Any number of electronic control modules may be operatively connected to the vehicle network 100.

In one embodiment a wireless transceiver module 110 is operatively connected to a vehicle network 100 and it is the wireless transceiver module 110 which is in operative communication with one or more wearable devices such as wearable ear piece 12A, 12B. Once a wearable device 12A, 12B or the vehicle 2 has identified a user, then that user is permitted to give instructions which are translated into commands which are communicated over the vehicle network 100 to an appropriate system or component of the vehicle or to communicate data such as data from one or more sensors of the wearable device 12A, 12B. Data from the wearable device may be used by any number of different electronic control modules or electronic control units 102, 104, 106, 108 connected to the vehicle network 100 to perform any number of different vehicle functions.

Figure 5:
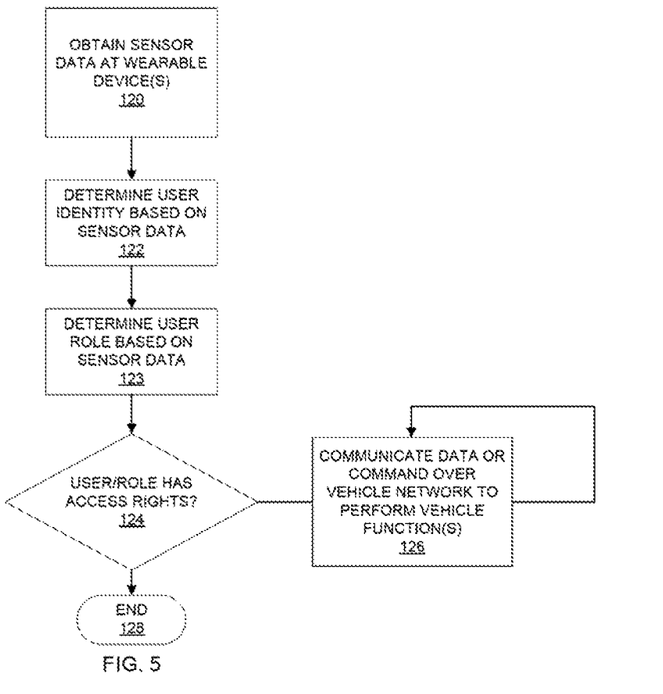

FIG. 5 illustrates one example of a methodology. As shown in FIG. 5 at step 120 sensor data is obtained at one or more wearable devices. As previously explained the sensor data can be of any number of types. For example, the sensor data may be voice data or other biometric data. In step 122 a determination is made of the user identity based on the sensor data. Where the sensor data is voice data this determination may be as the result of a voice print or voice sample analysis. Any number of different products or components may be used to perform this analysis. Examples of commercial products for performing such functionality include Nuance VocalPassword, Voice IT, and numerous others. It should be further understood that other types of biometric data may be used. For example, where the wearable device is a pair of glasses then retina identification and authentication may be used. Where the wearable device is a pair of gloves than finger print analysis may be used. The determination of the user identify based on sensor data may be performed in one of several different locations based on the type of analysis and available computational resources. For example, the determination may be performed on or at the wearable device itself. Alternatively, the determination may be performed on or at the vehicle. Alternatively still, the determination may be performed by a mobile device such as a smart phone which is in operative communication with either the wearable device(s) or the vehicle, or both. Where determinations are made by the wearable it may be performed by the intelligent control system.

Once the individual has been identified, in step 123, the role of the user may be determined based on sensor data or other data associated with one or more wearable devices. This determination may be performed in various ways. For example, data from one or more inertial sensors may be correlated with vehicle data. Thus, if sensor data shows a downward movement and the vehicle shows opening of a door, then this data may be correlated and a determination may be made that the user wearing the wearable device is the user that opened the door and entered the vehicle. If the door is the driver's door, the system may make the determination that the user is the driver. Similarly, if sensor data shows movement of the hands or wrists of a user consistent with the placing their hands on the steering wheel then it may be inferred that user is the driver. Similarly if the sensor data includes image information such as from a camera associated with the wearable device, that information may be processed to determine the role of the user. In addition, the wearable device may be used to determine a location such as a seat location of a user within the vehicle. The role may then be determined based on the seat location.

Once the individual has been identified or recognized, in step 124 a determination is made as to whether the user has access rights. In one implementation, if the user is identified then the user has appropriate access rights. In alternative implementations, identifying the user does not necessarily give the individual all rights. Where the user has appropriate access rights or none are required, in step 126 data or commands may be communicated over the vehicle network to perform various vehicle functions. Data from the wearable device(s) may be used by any electronic control modules associated with the vehicle network to provide input to be used in any number of different decision-making processes. Similarly, commands may be given from the user to the vehicle using the wearable device such as when the wearable device is an earpiece and the commands may be given through voice input from the user.

It is further contemplated that particular commands may be automatically communicated based on the identity of the user. In other words, once the user has been identified the vehicle may perform one or more vehicle functions automatically based on the identity of the user. These functions may be any number of different functions previously discussed or other functions including functions that grant access or deny access to the user.

According to another aspect, one or more wearable devices may be used to identify an individual and the role of the individual as a driver or passenger of a vehicle. Once the driver has been identified a number of different actions may be taken by vehicle control systems. This may include automatically adjusting various settings within the vehicle based on user preferences. Thus, for example, seats may be adjusted to the position preferred by the user including through adjusting the seat forward or back, upward or downward, or adjusting, the angle of the seat. Similarly, the position of the rearview mirrors or other mirrors may be adjusted based on preferences associated with the particular driver. In addition, steering wheel position may be adjusted based on preferences associated with the particular driver. These various adjustments may be performed in various ways including through the use of servo motors or other types of motors, switches, or other actuators.

Similarly, various other types of settings may be stored which are associated with a particular individual whether driver or passenger. These may include navigation settings. Thus, navigation settings associated with a particular individual may be used. Thus, for example where an individual has previously identified a particular location (such as "Peter's house ") within the navigation system, those particular locations may be associated with the individual and automatically available. Note, that locations associated with one or more passengers may also be added to the system as well.

Other types of settings such as radio station or satellite radio presets or favorites may also be loaded. Other settings associated with an entertainment system or infotainment system may also be made. Again, these settings may be associated with the driver and/or one or more passengers.

Various other types of settings may be also be associated with a user. The settings may include door lock settings, climate settings, light settings, and any number of other personalized settings. The settings may further include other navigation settings and preferences, camera settings and preferences, vehicle settings and preferences, system settings and preferences, phone settings and preferences, info settings and preferences, audio settings, and preferences, and any number of other electronic or electro-mechanical settings, preferences, or adjustments which may be made by the vehicle.

Where there is more than one individual within the vehicle with a wearable device, it is contemplated that a determination may be made as to which individual is the driver and which individual or individuals are passengers. It is contemplated that this determination may be made in any number of ways. For example, where the wearable device is in the form of two earpieces, it is contemplated that the position of a particular user may be found within the vehicle by using directional range finding or similar techniques to determine position. Where the wearable device includes one or more inertial sensors, it is contemplated that the identity of one or more users may be determined based on movement of the user. For example, where the wearable device is a watch, movement of the wrist consistent with placing the hand on a steering wheel may be indicative of which user is the driver. Where the wearable device is a set of earpieces, the timing of the movement of the head relative to the opening and closing of the driver's door may be indicative of which user is the driver. Similarly, the timing of the movement of the head relative to the opening and closing of a passenger's door may be indicative of which user is the passenger. In addition, a single individual may be associated with the vehicle as a primary driver with one or more other individuals associated as secondary drivers. Alternatively, the vehicle or wearable device may prompt one or more individuals to ask "Who is driving" or "Are you driving" or "Who is driving, Peter or Jim Senior?"

According to another aspect, information from a wearable device may be used to improve comfort and safety of a driver or passenger by suggesting user settings for optimum comfort and/or safety. Where a wearable device includes one or more physiological sensors and/or other physiological data or biometric data is available, this data may be used to suggest specific user settings. For example, recommendations may be made for seat settings based on a known height of an individual, known measurements of their legs or torso, arm length, or other body measurements.

Similarly, where the wearable device contains music such as a plurality of audio files or playlists, this information may be communicated to the vehicle and based on this information the vehicle may determine a set of radio presets based, for example, on the type or types of music present on the wearable device.

One application of this aspect is when an individual wearing an appropriate wearable device enters a vehicle the first time, such as when selecting a vehicle to buy. Based on available biometric information from the wearable device, the vehicle may self-adjust to settings consistent with the known biometric information to increase the comfort of the individual, better accommodate the individual, and/or provide an enhanced initial experience with the vehicle. Similarly, if an individual prefers other settings than those recommended, information about those settings may be communicated to the wearable device, stored, and communicated to other vehicles or other devices which the driver may operate. It is also contemplated that in some applications, once a user has set vehicle settings in the manner desired by the user, the user may have the vehicle send those settings to the wearable device to be stored by the wearable device. In addition to the vehicle settings the data stored may include information about the make and/or model of vehicle and other information. Thus, the wearable device may store user settings for a vehicle which have previously been used in a vehicle such as the same vehicle or a different vehicle of the same or similar type. This may be especially convenient and enhance safety where an individual regularly drives different vehicles such as different rental vehicles, different fleet vehicles, or for other vehicles which are shared between multiple users.

Figure 6:
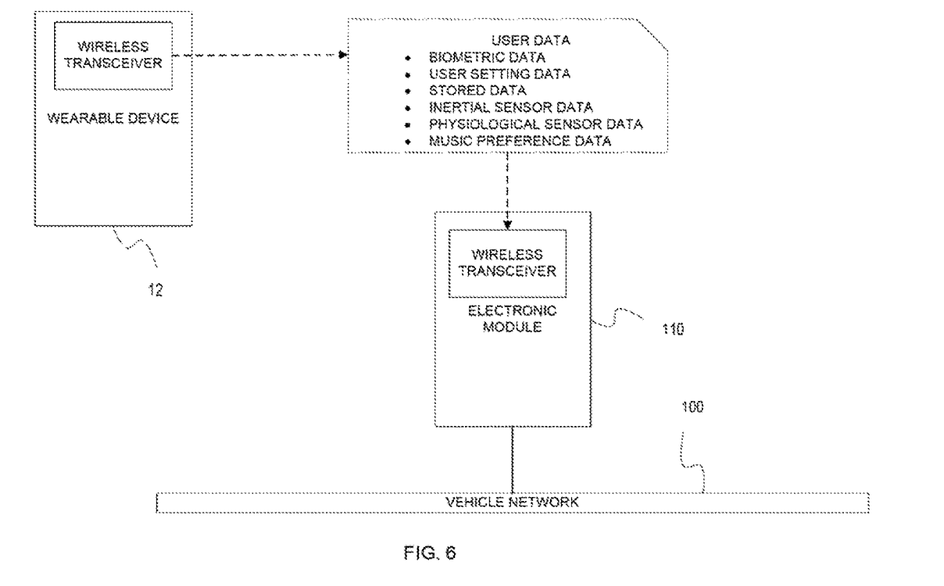
FIG. 6 illustrates another diagram of wearable devices communicating with a vehicle network.

FIG. 6 illustrates another example of a system. As shown in FIG. 6, a wearable device 12 includes a wireless transceiver. The wearable device may be an ear piece, a set of ear pieces, a watch, glasses, integrated into an article of clothing, or other type of wearable device. The wearable device 12 communicates user data to a wireless transceiver associated with an electronic module 110 of a vehicle. The user data may include biometric data, user setting data, stored data, inertial sensor data, physiological sensor data, music preference data, or other types of data. Such data may be translated into user settings of the vehicle and communicated to the appropriate modules over the vehicle network 100. The other modules may then provide for automatically adjusting one or more vehicle features or controlled based on the user settings.

Various methods, system, and apparatus have been shown and described relating to vehicles with wearable integration or communication. The present invention is not to be limited to these specific examples but contemplates any number of related methods, system, and apparatus and these examples may vary based on the specific type of vehicle, the specific type of wearable device, and other considerations.

What is claimed is:

1. A system comprising:
a vehicle, the vehicle comprising a vehicle network; and
a wireless earpiece worn by a user in operative communication with the vehicle network;
wherein the vehicle is configured to determine a role of the user and user settings for the vehicle from data received from the wireless earpiece and an action performed by the user on the vehicle, wherein the data includes inertial data from an inertial sensor of the wireless earpiece;
wherein the wireless earpiece is configured to confirm an identity of the user using the data stored on the wireless earpiece; and
wherein the vehicle is further configured to implement the user settings in accordance with the role of the user in response to the confirmation of the identity of the user by the wireless earpiece.

2. The system of claim 1 wherein the data includes biometric data.

3. The system of claim 2 wherein the biometric data is determined using one or more sensors of the wireless earpiece.

4. The system of claim 3 wherein the one or more sensors include a physiological sensor.

5. The system of claim 2 wherein the biometric data comprises biometric data stored on the wireless earpiece.

6. The system of claim 2 wherein the user settings comprise seat settings and wherein the biometric data includes height information.

7. The system of claim 1 wherein the user settings comprise entertainment settings and wherein the data comprises entertainment data.

8. The system of claim 7 wherein the entertainment settings include radio presets and wherein the entertainment data comprises music preferences.

9. The system of claim 6 wherein recommendations associated with the seat settings are provided by the wireless earpiece in accordance with the biometric data of the user.

10. A method for adjusting one or more user settings associated with a vehicle based on user data from a wireless earpiece worn by a user, the method comprising:
    acquiring, by the vehicle, the user data stored on the wireless earpiece worn by the user via a wireless linkage between the vehicle and the wireless earpiece, wherein the user data includes data from an inertial sensor of the wireless earpiece;
    based on the user data, confirming, by the wireless earpiece, an identity of the user;
    based on the user data, determining, by the vehicle, the one or more user settings;
    based on the user data and vehicle data, determining, by the vehicle, a role of the user; and
    automatically adjusting, by the vehicle, one or more vehicle features based on the one or more user settings in accordance with the role of the user in response to the confirmation of the identity of the user by the wireless earpiece.

11. The method of claim 10 wherein the user data comprises biometric data.

12. The method of claim 10 wherein the user data comprises music preference data.

13. The method of claim 12 wherein the user settings include entertainment system settings.

14. The method of claim 13 wherein the entertainment system settings include radio preset settings.

15. The method of claim 11 wherein the confirmation of the identity of the user is further determined from answers provided by the user in response to questions communicated to the user by the wireless earpiece, wherein the questions are associated with activities of the user.

* * * * *